United States Patent
Nguyen et al.

(10) Patent No.: US 11,896,945 B2
(45) Date of Patent: *Feb. 13, 2024

(54) HIGH SURFACE AREA COATINGS FOR SOLID-PHASE SYNTHESIS

(71) Applicant: MICROSOFT TECHNOLOGY LICENSING, LLC, Redmond, WA (US)

(72) Inventors: Bichlien Hoang Nguyen, Seattle, WA (US); Karin Strauss, Seattle, WA (US); Hsing-Yeh Parker, Woodinville, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/597,799

(22) Filed: Oct. 9, 2019

(65) Prior Publication Data

US 2021/0106967 A1  Apr. 15, 2021

(51) Int. Cl.
  *B01J 19/00* (2006.01)
  *C07K 1/04* (2006.01)
  (Continued)

(52) U.S. Cl.
  CPC .......... *B01J 19/0046* (2013.01); *C07K 1/042* (2013.01); *C25D 5/16* (2013.01); *C25D 5/48* (2013.01);
  (Continued)

(58) Field of Classification Search
  CPC . B01J 19/00; C07K 1/04; C25D 17/10; C25D 5/16; C25D 5/48
  (Continued)

(56) References Cited

U.S. PATENT DOCUMENTS

| 4,668,777 A | 5/1987 | Caruthers et al. |
| 4,973,679 A | 11/1990 | Caruthers et al. |

(Continued)

FOREIGN PATENT DOCUMENTS

| EP | 1629884 A1 | 3/2006 |
| WO | 0061282 A1 | 10/2000 |

(Continued)

OTHER PUBLICATIONS

Terrett, Nicholas K.., "Solid Phase Library Chemistry", In Book Combinatorial Chemistry, Dec. 31, 1998, pp. 125-126.

(Continued)

*Primary Examiner* — Tahseen Khan
(74) *Attorney, Agent, or Firm* — Benjamin Keim; Newport IP, LLC

(57) ABSTRACT

High surface area coatings are applied to solid substrates to increase the surface area available for solid-phase synthesis of polymers. The high surface area coatings use three-dimensional space to provide more area for functional groups to bind polymers than an untreated solid substrate. The polymers may be oligonucleotides, polypeptides, or another type of polymer. The solid substrate is a rigid supportive layer made from a material such as glass, a silicon material, a metal material, and plastic. The coating may be thin films, hydrogels, microparticles. The coating may be made from a metal oxide, a high-κ dielectric, a low-κ dielectric, an etched metal, a carbon material, or an organic polymer. The functional groups may be hydroxyl groups, amine groups, thiolate groups, alkenes, n-alkenes, alkalines, N-Hydroxysuccinimide (NHS)-activated esters, polyaniline, aminosilane groups, silanized oxides, oligothiophenes, and diazonium compounds. Techniques for applying coatings to solid substrates and attaching functional groups are also disclosed.

20 Claims, 8 Drawing Sheets

(51) Int. Cl.
  *C25D 17/10* (2006.01)
  *C25D 5/48* (2006.01)
  *C25D 5/16* (2006.01)

(52) U.S. Cl.
  CPC ....... *C25D 17/10* (2013.01); *B01J 2219/0059* (2013.01); *B01J 2219/00497* (2013.01); *B01J 2219/00596* (2013.01); *B01J 2219/00612* (2013.01); *B01J 2219/00722* (2013.01); *B01J 2219/00725* (2013.01)

(58) Field of Classification Search
  USPC ....................................................... 530/334
  See application file for complete search history.

(56) References Cited

U.S. PATENT DOCUMENTS

| | | | |
|---|---|---|---|
| 5,605,662 | A | 2/1997 | Heller et al. |
| 6,017,696 | A | 1/2000 | Heller |
| 6,051,380 | A * | 4/2000 | Sosnowski ........... B01J 19/0046 435/6.11 |
| 6,093,370 | A | 7/2000 | Yasuda et al. |
| 6,423,172 | B1 * | 7/2002 | McArdle .................. B05D 7/00 156/305 |
| 6,444,111 | B1 | 9/2002 | Montgomery |
| 6,451,191 | B1 | 9/2002 | Bentsen et al. |
| 6,610,479 | B1 | 8/2003 | Lundeberg et al. |
| 6,951,682 | B1 | 10/2005 | Zebala |
| 6,994,972 | B2 | 2/2006 | Bardhan et al. |
| 7,115,531 | B2 | 10/2006 | Shaffer et al. |
| 7,172,864 | B1 | 2/2007 | Heller et al. |
| 7,268,200 | B2 | 9/2007 | Townsend et al. |
| 7,385,050 | B2 | 6/2008 | Dellinger et al. |
| 7,417,139 | B2 | 8/2008 | Dellinger et al. |
| 7,494,797 | B2 | 2/2009 | Mueller et al. |
| 8,053,774 | B2 | 11/2011 | Dubin et al. |
| 8,278,121 | B2 | 10/2012 | Dubin et al. |
| 8,697,605 | B2 | 4/2014 | Gao et al. |
| 8,940,143 | B2 | 1/2015 | Dubin et al. |
| 9,745,628 | B2 | 8/2017 | Gao et al. |
| 10,035,147 | B2 | 7/2018 | Dubin et al. |
| 10,059,929 | B2 | 8/2018 | Efcavitch et al. |
| 10,294,526 | B2 | 5/2019 | Gao et al. |
| 2002/0052125 | A1 * | 5/2002 | Shaffer, II ......... H01L 21/76813 438/780 |
| 2002/0142339 | A1 | 10/2002 | Bardhan et al. |
| 2003/0059929 | A1 * | 3/2003 | Heller .................. C12Q 1/6837 435/287.2 |
| 2004/0152085 | A1 | 8/2004 | Terlesky et al. |
| 2004/0238369 | A1 | 12/2004 | Southern et al. |
| 2006/0046262 | A1 | 3/2006 | Mauritz |
| 2006/0102471 | A1 | 5/2006 | Maurer et al. |
| 2006/0194214 | A1 | 8/2006 | Church et al. |
| 2006/0275927 | A1 | 12/2006 | Dubin et al. |
| 2008/0070803 | A1 | 3/2008 | Egeland |
| 2009/0000957 | A1 | 1/2009 | Dubin et al. |
| 2009/0075840 | A1 | 3/2009 | Myerson et al. |
| 2009/0325817 | A1 * | 12/2009 | Gao ........................ C40B 50/18 506/16 |
| 2012/0029056 | A1 | 2/2012 | Alevizos et al. |
| 2013/0098771 | A1 | 4/2013 | Emig et al. |
| 2013/0281324 | A1 | 10/2013 | Gouliaev et al. |
| 2018/0267032 | A1 | 9/2018 | Maurer et al. |
| 2020/0199662 | A1 * | 6/2020 | Strauss ................... C40B 50/18 |
| 2020/0384434 | A1 | 12/2020 | Nguyen et al. |
| 2021/0047669 | A1 | 2/2021 | Nguyen |
| 2021/0071170 | A1 | 3/2021 | Nguyen et al. |
| 2023/0151411 | A1 | 5/2023 | Strauss et al. |

FOREIGN PATENT DOCUMENTS

| | | | |
|---|---|---|---|
| WO | 02097112 | A2 | 12/2002 |
| WO | 2008051454 | A1 | 5/2008 |
| WO | 2017142913 | A1 | 8/2017 |
| WO | 2017156218 | A1 | 9/2017 |
| WO | 2017176541 | A1 | 10/2017 |
| WO | 2017223517 | A1 | 12/2017 |
| WO | 2018119253 | A1 | 6/2018 |

OTHER PUBLICATIONS

"International Search Report and Written Opinion Issued in PCT Application No. PCT/US2019/066106", dated Feb. 20, 2020, 13 Pages.

Bi, et al., "Building Addressable Libraries: The Use of "Safety-Catch" Linkers on Microelectrode Arrays", In Journal of the American Chemical Society vol. 132, Issue 49, Nov. 19, 2010, pp. 17405-17407.

Egeland, et al., "Electrochemically Directed Synthesis of Oligonucleotides for DNA Microarray Fabrication", Published in Nucleic Acids Research, vol. 33, Issue 14, Aug. 5, 2005, pp. 1-7.

Hart, et al., "Synthesis and Characterization of trans-Dichlorotetrakis (imidazole)cobalt(III) Chloride: A New Cobalt(III) Coordination Complex with Potential Prodrug Properties", In Journal Bioinorganic Chemistry and Applications,vol. 2018, Article ID 4560757, Sep. 3, 2018, 7 Pages.

Heffern, et al., "Cobalt Derivatives as Promising Therapeutic Agents", In Journal Current opinion in chemical biology, vol. 17,Issue 2, 2013, pp. 189-196.

Lee, et al., "Terminator-free Template-independent Enzymatic DNA Synthesis for Digital Information Storage", Published in Nature Communications, vol. 10, Article No. 2383, Jun. 3, 2019, pp. 1-12.

Motea, et al., "Terminal Deoxynucleotidyl Transferase: The Story of a Misguided DNA Polymerase", Published in Biochimica et Biophysica Acta (BBA)—Proteins and Proteomics, vol. 1804, Issue 5, May 2010, pp. 1151-1166.

Palluk, et al., "De novo DNA Synthesis Using Polymerasenucleotide Conjugates", Published in Nature Biotechnology vol. 36, Issue 7, Jul. 2018, 24 Pages.

Richey, et al., "Mg Anode Corrosion in Aqueous Electrolytes and Implications for Mg-Air Batteries", In Journal of The Electrochemical Society, vol. 163, Issue 6, 2016, pp. A958-A963.

Shaw, et al., "Photoredox Catalysis in Organic Chemistry", In the Journal of Organic Chemistry ,vol. 81, Issue 16, Aug. 1, 2016, pp. 6898-6926.

Kosuri, et al., "Large-Scale de Novo DNA Synthesis: Technologies and Applications", In Journal of Nature Methods, vol. 11, Issue 5, May 2014, pp. 499-507.

Zheng, et al., "A Redox-Sensitive Resin Linker for the Solid Phase Synthesis of C-Terminal Modified Peptides", In the Journal of Organic Chemistry,vol. 64, Dec. 9, 1998, Issue 1, pp. 156-161.

Devor, et al., "Strategies for Attaching Oligonucleotides to Solid Supports", Integrated DNA Technologies v6, 2014, pp. 1-22.

Rothstein, et al., "Solid-Phase Supports for Oligo Synthesis", Retrieved from: https://www.genengnews.com/magazine/181/solid-phase-supports-for-oligo-synthesis/4096/, Retrieved Date: Jun. 20, 2019, 08 Pages.

Sonawane, et al., "Surface Modification Chemistries of Materials Used in Diagnostic Platforms with Biomolecules", In Journal of Chemistry, vol. 2016, Article ID 9241378, May 25, 2016, pp. 1-19.

Zhang, et al., "DNA Molecules Site-Specific Immobilization and their Applications", In Central European Journal of Chemistry, vol. 12, Issue 10, Oct. 1, 2014, pp. 977-993.

"International Search Report and Written Opinion Issued in PCT Application No. PCT/US20/051345", dated Dec. 9, 2020, 13 Pages.

Pirrung, Michael C. , "How to Make a DNA Chip", In Journal of Angewandte Chemie International Edition, vol. 41, Issue 8, Apr. 15, 2002, pp. 1277-1289.

"International Search Report and Written Opinion Issued in PCT Application No. PCT/US2020/029180", dated Jul. 16, 2020, 10 Pages.

"Non Final Office Action Issued in U.S. Appl. No. 16/230,787", dated Feb. 24, 2021, 07 Pages.

"Final Office Action Issued in U.S. Appl. No. 16/230,787", dated Aug. 18, 2021, 14 Pages.

(56) References Cited

OTHER PUBLICATIONS

"Non Final Office Action Issued in U.S. Appl. No. 16/435,463", dated Apr. 18, 2022, 9 Pages.
"Non Final Office Action Issued in U.S. Appl. No. 16/543,433", dated May 27, 2022, 9 Pages.
"International Search Report and Written Opinion Issued in PCT Application No. PCT/US20/037104", dated Sep. 28, 2020, 10 Pages.
"Non Final Office Action Issued in U.S. Appl. No. 16/230,787", dated Mar. 17, 2022, 19 Pages.
Usui, et al., "A Cell Microarray Format: A Peptide Release System Using a Photo-Cleavable Linker for Cell Toxicity and Cell Uptake Analysis", In Book of Peptide Microarrays:Methods and Protocols, Chapter 15, 2016, pp. 199-210.
"Final Office Action Issued in U.S. Appl. No. 16/230,787", dated Jul. 28, 2022, 19 Pages.
Atrash, et al., "A pH Cleavable Linker for Zone Diffusion Assays and Single Bead Solution Screens in Combinatorial Chemistry", In Journal of Chemical Communications, vol. 15, Jan. 1, 1997, pp. 1397-1398.
Routledge, et al., "The Use of a Dithiane Protected Benzoin Photolabile Safety Catch Linker for Solid-Phase Synthesis", In Journal of Tetrahedron letters, vol. 38, Issue 7, Feb. 17, 1997, pp. 1227-1230.
Russell, et al., "Thermally Cleavable Safety-catch Linkers for Solid Phase Chemistry", In Journal of Tetrahedron Letters, vol. 41, Issue 27, Jul. 1, 2000, pp. 5287-5290.
"Notice of Allowance Issued in U.S. Appl. No. 16/230,787", dated Oct. 24, 2022, 11 Pages.
"Non Final Office Action Issued in U.S. Appl. No. 17/695,734", dated Oct. 18, 2022, 10 Pages.
"Final Office Action Issued in U.S. Appl. No. 16/435,363", dated Nov. 10, 2022, 17 Pages.
Moore, et al., "Selective Release of DNA from the Surface of Indium-Tin Oxide Thin Electrode Films using Thiol-Disulfide Exchange Chemistry", vol. 79, Issue 5, Mar. 1, 2007, pp. 2050-2057.
"Final Office Action Issued in U.S. Appl. No. 17/695,734", dated Feb. 9, 2023, 9 Pages.
"Notice of Allowance Issued in U.S. Appl. No. 16/543,433", dated Mar. 29, 2023, 7 Pages.
"Notice of Allowance Issued in U.S. Appl. No. 16/543,433", dated Apr. 14, 2023, 6 Pages.
"Non Final Office Action Issued in U.S. Appl. No. 16/435,363", dated Mar. 8, 2023, 10 Pages.
"Non Final Office Action Issued in U.S. Appl. No. 17/815,380", dated Mar. 9, 2023, 8 Pages.
Kim, et al., "Hierarchical gene synthesis using DNA microchip oligonucleotides", In Journal of Biotechnology, vol. 151, Issue 4, Feb. 20, 2011, pp. 319-324.
"Final Office Action Issued in U.S. Appl. No. 16/435,363", dated Nov. 7, 2023, 16 Pages.

* cited by examiner

HIGH SURFACE AREA COATINGS FOR SOLID-PHASE SYNTHESIS

BACKGROUND

Solid-phase synthesis creates polymers by growing the polymers on a solid substrate in a step-by-step process. Solid phase synthesis can be more efficient, faster, and simpler than synthesis in a liquid state. The solid substrate may be functionalized by attaching functional groups that bond to monomeric subunits of the polymers. After synthesis is complete, the polymers are separated from the solid substrate by breaking the bonds to the functional groups.

Many types of polymers can be created by solid-phase synthesis. There are known solid phase synthesis techniques for oligonucleotides, polypeptides, and other polymers. The specific solid-phase synthesis technique of course differs according to the type of polymer. Oligonucleotides, for example, may be synthesized using the well-known phosphoramidite method in which phosphoramidite building blocks are sequentially coupled to a growing oligonucleotide chain in a particular sequence.

One factor that affects the number of polymers synthesized per-batch is the number of available functional groups. As the number of functional groups increases, the number of potential sites for solid-phase synthesis also increases. The type of solid substrate, the type of functional group, and the technique for functionalizing the solid substrate all affect the number of available functional groups. However, for any configuration there is a maximum density of functional groups per unit of surface area (e.g., $mm^2$) of the solid substrate.

Current solid-phase synthesis techniques are sufficient for many applications. However, there are new uses for polymers that can benefit from improvements to solid-phase synthesis. For example, deoxyribose nucleic acid (DNA) is used to store digital information by synthesizing artificial DNA strands in which the order of nucleotide bases encodes binary digits. Using DNA, or any other polymer, for digital information storage can benefit from increased throughput and decreased cost. The following disclosure is made with respect to these and other considerations.

SUMMARY

This disclosure provides structures and methods of making "stacks" for use in solid-phase synthesis of polymers. The quantity of polymers synthesized per unit area of solid substrate is increased by applying a coating with a three-dimensional structure that provides a high surface area. The coating provides more surface area than an un-coated solid substrate. Providing additional surface area without increasing the size of the solid substrate increases the quantity of polymers synthesized thereby increasing polymer density which can increase throughput and decrease cost.

Solid-phase synthesis with higher polymer density produces more polymers per unit area. A larger number of polymers, or "copy number" in the case of DNA, provides multiple benefits. It improves detection by increasing signal strength. It also, by creating a larger sample pool, reduces the impact of individual synthesis errors on a consensus polymer sequence. Furthermore, higher polymer density allows for the construction of smaller polymer synthesizers with the same capacity as polymer synthesizers using a larger but uncoated solid substrate.

A stack for solid-phase polymer synthesis includes at least a solid substrate, a coating with a three-dimensional structure, and functional groups for attaching the polymers. The solid substrate provides structural support and rigidity. Examples of solid substrates include, but are not limited to, glass, a silicon material, a metal material, and plastic.

Examples of the coatings include, but are not limited to, a metal oxide, a high-κ dielectric, a low-κ dielectric, an etched metal, a carbon material, an organic polymer, or combinations thereof. The coatings may be thin films, hydrogels, microparticles, or other structures. The coating may be applied by a number of techniques including, but not limited to, oxidizing, electroplating, annealing, spin coating, dip coating, spray coating, sputtering, in-situ polymerization, and the sol-gel process.

The functional groups may be inherently present on the coating (i.e., as part of its molecular structure) or added to the coating through functionalization. Examples of functional groups include, but are not limited to, hydroxyl groups, amine groups, thiolate groups, alkenes, n-alkenes, alkalines, N-Hydroxysuccinimide (NHS)-activated esters, polyaniline, aminosilane groups, silanized oxides, oligothiophenes, and diazonium compounds. Functional groups, if not inherently present on the coating, may be attached to the coating by silanization, chemical grafting, electro-grafting, photochemical grafting, electrochemical polymerization, or other techniques.

In some implementations, the solid substrate may be patterned. Patterning of the solid substrate may be used to create separate reaction environments on the surface of the solid substrate by establishing boundaries between regions of the coating. Patterning may be performed by addition of a metal to the surface of the solid substrate. In some implementations, the solid substrate may be an integrated circuit (IC) such as a complementary metal-oxide-semiconductor (CMOS). Patterning may also be used to expose electrodes embedded within the solid substrate or deposited below the solid substrate. In implementations in which the solid substrate includes electrodes, the electrodes can function to drive some types of polymer synthesis reactions.

In some implementations, the coating may be patterned to expose the underlying solid substrate. This may further increase the surface area of the coating by creating troughs or pits. The troughs, pits, or similar structures may be used to localize groups of polymers and reduce cross-contamination by spatially isolating available DNA binding sites. Patterning the coating can also expose regions on the surface of the solid substrate such as regions on which electrodes are located.

Surface area can be further increased by adding a second coating. The second coating may cover the first coating and any exposed regions of the solid substrate. The second coating may have a higher surface area than the first coating. Examples of suitable materials for the second coating include microparticles, aerogels, and organic polymers. Functional groups may be present on the first coating and on the second coating. The second coating may be applied by techniques including, but not limited to, annealing, spin coating, dip coating, spray coating, sputtering, and the sol-gel process.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Structures shown in the figures are representative and not necessarily to scale.

DETAILED DESCRIPTION

Figure 1:
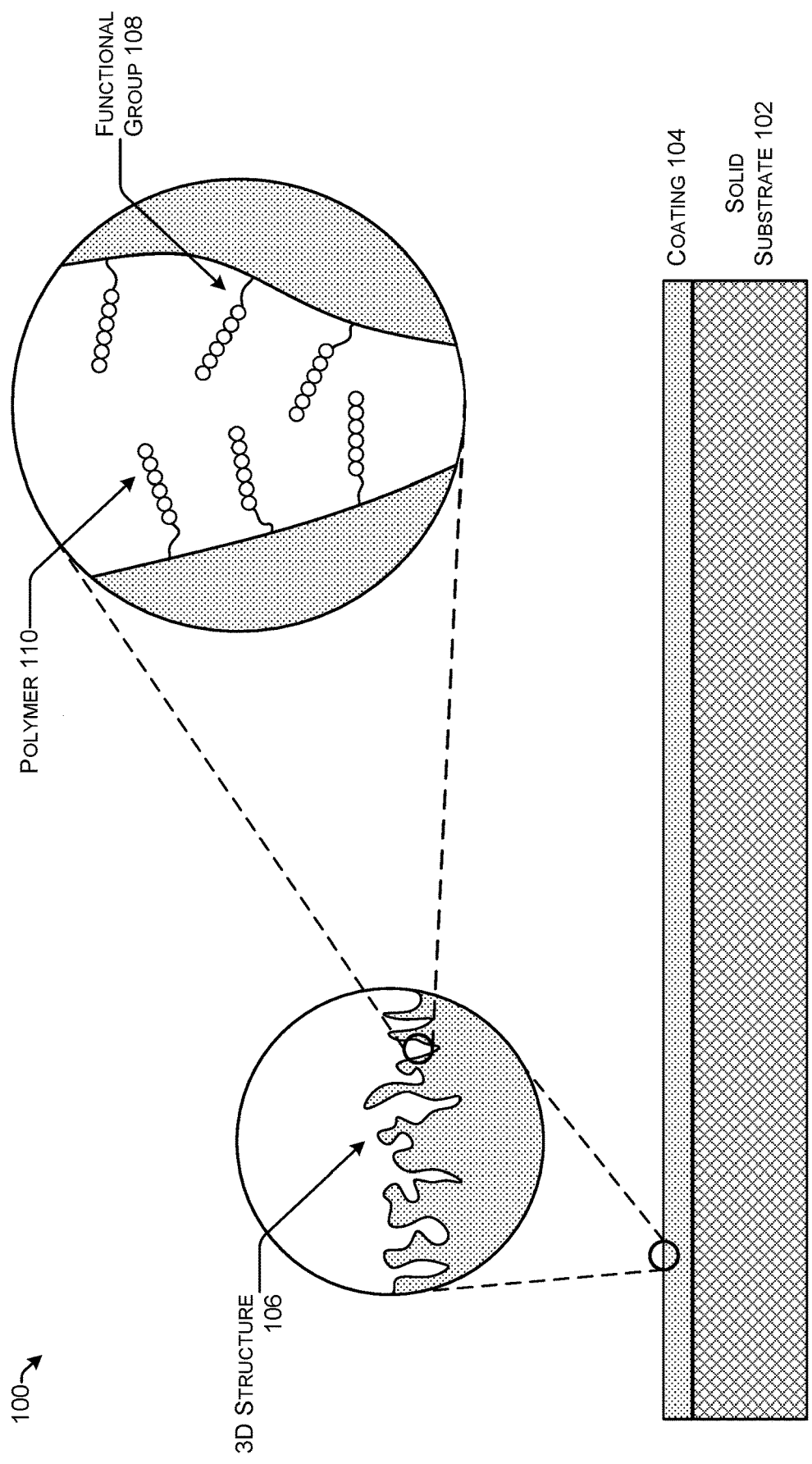
FIG. 1 shows one example of a stack for solid-phase polymer synthesis with a coating that has a three-dimensional structure.

High surface area coatings use the three-dimensional space above a substantially flat solid substrate to increase the surface area available for solid phase synthesis of polymers. The surface of any solid substrate will have some level of texture at a molecular level. However, for most solid substrates the usable surface area for polymer synthesis can be measured in two dimensions (i.e., the surface is effectively flat). For example, a solid substrate surface of 2 mm×3 mm provides a surface area of 6 mm². A high surface area coating applied to that 6 mm² area of the solid substrate provides more than 6 mm² of surface to synthesize polymers. Thus, the available surface area for synthesizing polymers per two-dimensional surface area of the solid substrate is increased by addition of a high surface area coating. Depending on the type of coating, the available surface area may be increased by amounts such as 1.1×, 1.2×, 1.3×, 1.4×, 1.5×, 2×, 3×, 4×, 5×, 10×, 25×, 50×, 100×, or more. The available surface area may be increased within the range of 1.1-100×, 1.1-50×, 1.1-25×, 1.1-10×, 1.1-5×, 1.1-4×, 1.1-3×, 1.1-2×, 1.1-1.5×, 1.1-1.4×, 1.1-1.3×, 1.1-1.2×, or any narrower included range.

The stacks described in this disclosure may be used for solid phase synthesis of many different types of polymers. As used herein, a polymer is any molecule formed from one or more types of repeating monomer subunits. Polymers include biological polymers and artificial organic polymers.

Biological polymers are naturally occurring polymers such as oligonucleotides and polypeptides. Oligonucleotides include both DNA, ribonucleic acid (RNA), and hybrids containing mixtures of DNA and RNA. DNA includes nucleotides with one combination of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases. Polypeptides have multiple amino acids linked via amide bonds, also known as peptide bonds. Amino acids as used herein includes all 20 standard amino acids, all 22 natural amino acids, non-proteinogenic amino acids, and D-isomers.

Artificial organic polymers are non-natural polymers that contain the element carbon. Examples of artificial organic polymers include peptide nucleic (PNA) and threose nucleic acid (TNA).

The stacks described herein are also compatible with many different polymerization techniques. For example, various implementations of the stacks may be used for phosphoramidite-based DNA synthesis, enzymatic DNA synthesis, or both. Phosphoramidite-based synthesis uses a cycle of four different monomer mixtures to add each individual nucleoside in a 3' to 5' synthesis direction. Phosphoramidite synthesis is performed in a solution of an organic solvent such as acetonitrile. Enzymatic synthesis of DNA uses a template-independent DNA polymerase, terminal deoxynucleotidyl transferase (TdT), which is an enzyme that evolved to rapidly catalyze the linkage of naturally occurring nucleosides in a 5' to 3' direction. TdT adds nucleotides indiscriminately so it is stopped from continuing unregulated synthesis by various techniques such a tethering the TdT, creating variant enzymes, and using nucleotides that include reversible terminators to prevent chain elongation. Enzymatic synthesis is performed in an aqueous solution.

Solid-phase synthesis of peptides (SPSS) is another technique for synthesizing polymers that may be performed on the stacks provided in this disclosure. SPSS allows the rapid assembly of a peptide chain through successive reactions of amino acid derivatives on an insoluble porous support (i.e., a stack). The general SPSS procedure is one of repeated cycles of alternate N-terminal deprotection and coupling reactions. The cycles are repeated until the desired sequence has been synthesized. SPSS cycles may also include capping steps which block the ends of unreacted amino acids from reacting.

FIG. 1 shows one example of stack 100 for use in solid-phase polymer synthesis. The stack 100 includes a solid substrate 102 and a coating 104. The coating 104 has a three-dimensional (3D) structure 106 that provides more surface area than the solid substrate 102. The surface area provided by the 3D structure 106 of the coating 104 is covered with functional groups 108. The functional groups 108 are attached through functionalization or inherently present based on the composition of the coating 104. Polymers 110 are synthesized on the functional groups 108.

Polymer synthesis may proceed according to conventional solid-phase synthesis techniques known to those of ordinary skill in the art. Following the completion of synthesis, the polymers 110 may be released from the stack 100 by cleaving the functional group 108, breaking a bond connecting the polymer 110 to the functional group 108, or breaking a bond connecting the functional group 108 to the surface of the coating 104. Techniques for separating a polymer from a solid-phase substrate are known to those of ordinary skill in the art. Illustrative linkers for attaching polymers to solid substrates and techniques for cleaving polymers from solid substrates are described in U.S. patent application Ser. No. 16/230,787 filed on Dec. 21, 2018 with the title "Selectively Controllable Cleavable Linkers."

The solid substrate 102 is a solid object having one or more rigid surfaces. At least one surface of the substrate is substantially flat providing a two-dimensional surface. The solid substrate 102 can have any size and shape. The solid substrate 102 may be part of a larger object formed from the same or different material. The solid substrate 102 can be comprised of any one or combination of glass, a silicon material, a metal material, and plastic.

In some implementations, the solid substrate 102 is formed from glass. As used herein, glass is a non-crystalline, amorphous solid. Glass may be soda lime glass or borosilicate glass which are both commonly used in glass slides. One preparation of glass that may be used for solid-phase synthesis is porous glass such as controlled pore glass (CPG). CPG is either in the form of ground irregularly shaped particles with broad particle size distribution or spherical beads with narrower particle size distribution. The particle size is about 75-130 μm or about 100-200 μm mesh. The pore size is in the range of 300 Å to 3000 Å. It is pre-derivatized to contain DNA synthesis linker functional groups (e.g., silane groups) on its surface. It may be used either as a bulk packed-bed column or embedded in a sintered plastic frit for traditional large-scale oligonucleotide synthesis. The column or frit provides a necessary structure to prevent migration of the small glass particles or beads.

Although porous glass provides a textured and functionalized surface, it has limitations that prevent use of conventional CPG as a solid substrate 102. CPG is not solid. If a layer of CPG is placed on the surface of a solid substrate 102, the particles or beads will flow off of the flat surface. A further limitation for all types of glass is that functionalization is generally restricted to silanization which adds silane groups containing terminal alcohol groups. Silane groups are not suitable functional groups for some types of polymer synthesis. Thus, in some implementations, the solid substrate 102 is not glass.

Silicon materials comprise silicon (Si), silicon oxides, silicon nitrides, and combinations thereof. Silicon refers to solid, metallic silicon. Silicon oxides include silicon dioxide ($SiO_2$). Silicon nitrides include chemical compounds of the elements silicon and nitrogen. The most thermodynamically stable silicon nitride is $Si_3N_4$. Unless otherwise specified, as used herein silicon nitride refers to $Si_3N_4$.

Metal materials comprise metals, metal oxides, metal nitrides, and combinations thereof such as alloys of two or more metals. As used herein, metal materials do not include silicon materials. In some implementations, the metal is a period 4 transition metal. The period 4 transition metals are scandium (Sc), titanium (Ti), vanadium (V), chromium (Cr), manganese (Mn), iron (Fe), cobalt (Co), nickel (Ni), copper (Cu), and zinc (Zn). In some implementations, the metal is a metal from the boron group. The boron group of metals are aluminum (Al), gallium (Ga), indium (In), and thallium (Tl). In some implementations, the metal is a noble metal. Noble metals are gold (Au), platinum (Pt), silver (Ag), and palladium (Pd). In some implementations, the metal is stainless steel. Stainless steel is a steel alloy with a minimum of about 10.5% chromium content by mass and a maximum of about 1.2% carbon by mass. Metal oxides include oxides of any of the metals listed above such. Metal nitride include nitrides of any of the metals listed above.

Plastics include thermoplastics, polymeric organosilicon compounds, synthetic rubber, polyimide, and combinations thereof. Thermoplastics include polycarbonates, polypropylene, polyethylene, and polyoxymethylene (POM). Polypropylene is a thermoplastic polymer that belong to the group of polyolefins. Polyethylene is a class of polymers of which most, but not all, have the chemical formula $(C_2H_4)_n$. Polymeric organosilicon compounds include polydimethylsiloxane (PDMS), also known as dimethylpolysiloxane or dimethicone. Synthetic rubber includes ethylene propylene diene monomer (EDPM) rubber and Viton®. There are multiple compositions of Viton® all of which are mixtures of one or more of copolymers of hexafluoropropylene (HFP) and vinylidene fluoride (VDF or VF2), terpolymers of tetrafluoroethylene (TFE), vinylidene fluoride (VDF), hexafluoropropylene (HFP), and perfluoromethylvinylether (PMVE). Polyimides include Kapton® which has the chemical formula poly (4,4'-oxydiphenylene-pyromellitimide).

Turning now to the coating 104, it is a different material than the solid substrate 102. The coating 104 can be different in the sense that it is chemically different from the material making up the solid substrate 102 or in the sense that it is physically different, but chemically identical (or substantially chemically similar). In some implementation, the coating 104 may be created by treating the surface of the solid substrate 102. In some implementations, the coating 104 may be physically associated with the surface of the solid substrate 102 (e.g., as stacked layers) or chemically associated with the surface of the solid substrate 102 (e.g., chemically bonded). The coating 104 may be applied to all or part of the surface of the solid substrate 102.

The coating 104 may be comprised of a metal oxide, a high-κ dielectric, a low-κ dielectric, an etched metal, a carbon material, an organic polymer, or combinations thereof. The coating 104 may be any one of thin films, hydrogels, microparticles, or other structures. A thin film is a layer of material ranging from fractions of a nanometer (monolayer) to several micrometers in thickness. A thin film may form a uniform layer or a porous layer. A hydrogel is a network of polymer chains that are hydrophilic. Hydrogels have a three-dimensional structure as a result of the hydrophilic polymer chains being held together by cross-links. A microparticle is a particle between about 1 and 1000 μm in size. As used herein, microparticle includes microspheres, nanoparticles, and nanospheres. A nanoparticle is a particle between about 1 and 1000 nm in size. Microspheres and nanospheres are microparticles and nanoparticles, respectively, with spherical or approximately spherical shapes.

Metal oxides are crystalline solids that contain a metal cation and an oxide anion. Examples of metal oxides include silicon dioxide ($SiO_2$), aluminum oxide ($Al_2O_3$), titanium oxide ($TiO_2$), barium titanate ($BaTiO_3$), barium zirconate ($BaZrO_3$), indium tin oxide (ITO), and hafnium dioxide ($HfO_2$). ITO is a ternary composition of indium, tin, and oxygen. ITO may be comprised of about 74% In, about 18% $O_2$, and about 8% Sn by weight.

High-κ and a low-κ dielectrics are inorganic substrates that have a higher or lower dielectric constant, respectively, than silicon dioxide ($SiO_2$). The dialectic properties are influenced not only by the chemical composition but also by the type of voids inside the material and the thickness of the material. Examples of high-κ dielectrics include hafnium silicate ($HfSiO_4$), zirconium silicate ($ZrSiO_4$), hafnium dioxide ($HfO_2$), and zirconium dioxide ($ZrO_2$). Examples of low-κ dielectrics include fluorine-doped silicon dioxide, organosilicate glass (OSG), porous OSG, polyimide, polynorbornenes, benzocyclobutene, polytetrafluoroethylene (PTFE), hydrogen silsesquioxane (HSQ), and methylsilsesquioxane (MSQ).

Etched metals may be made from noble metals, silicon (Si), nickel (Ni), copper (Cu), or any combination thereof. Metals may be etched electrochemically in an acid solution to create an etched metal.

The carbon material may be graphene, carbon nanotubes, diamond, boron-doped diamond, or any combination thereof. Graphene is an allotrope of carbon in the form of a single layer of atoms in a two-dimensional hexagonal lattice in which one atom forms each vertex. Carbon nanotubes are tubes made of carbon with diameters typically measured in nanometers. Carbon nanotubes include single-wall carbon nanotubes (SWCNTs) and multi-wall carbon nanotubes (MWCNTs) consisting of nested single-wall carbon nanotubes. Diamond is a solid form of the element carbon with its atoms arranged in a crystal structure called diamond cubic. Boron-doped diamond is synthetic diamond created by including boron atoms in the crystal structure. Boron-that doped diamond is an electrical conductor and, in some cases, a superconductor.

Suitable organic polymers include linear polymers and di-block copolymers. A linear polymer is a long continuous chain of carbon-carbon bonds with the remaining two valence bonds attached primarily to hydrogen or another relatively small hydrocarbon moiety. A di-block copolymer is a polymer consisting of two homopolymer subunits linked by covalent bonds. A di-block copolymer may be an alternating copolymer or periodic copolymer.

Polyacrylamide and polylysine are two examples of linear polymers. Polyacrylamide is a polymer (—$CH_2CHCONH_2$—) formed from acrylamide subunits. It can be synthesized as a simple linear-chain structure or cross-linked, typically using N,N'-methylenebisacrylamide. Polylysine refers to several types of lysine homopolymers, which may differ from each other in terms of stereochemistry and link position. α-Polylysine is a synthetic polymer, which can be composed of either L-lysine or D-lysine. "L" and "D" refer to the chirality at lysine's central carbon. This results in poly-L-lysine (PLL) and poly-D-lysine (PDL) respectively. ε-Polylysine (ε-poly-L-lysine, EPL) is typically produced as a homopolypeptide of approximately 25-30 L-lysine residues.

One class of linear polymers are polysaccharides such as agarose and chitosan. Polysaccharides are polymeric carbohydrate molecules composed of long chains of monosaccharide units bound together by glycosidic linkages. Agarose is made up of the repeating unit of agarobiose, which is a disaccharide made up of D-galactose and 3,6-anhydro-L-galactopyranose. Chitosan composed of randomly distributed β-(1→4)-linked D-glucosamine (deacetylated unit) and N-acetyl-D-glucosamine (acetylated unit).

A functional group 108 is a moiety capable of forming a chemical bond (e.g., a covalent bond and/or an electrostatic bond) with the coating 104 and also capable of forming a chemical bond, typically a covalent bond, with a monomer subunit of a polymer 110. In some configurations, functional groups 108 may also form chemical bonds with the solid substrate 102.

The functional group 108 may include a spacer (not shown). The spacer may be an organic spacer (e.g., an aliphatic spacer, an alkyl spacer, an aromatic spacer, an alkylene glycol, a polyethylene glycol, a carbohydrate (e.g., a sugar), or the like). In an implementation, the spacer may be a PEG spacer. PEG spacers are well-known inert spacers used in many biotechnological applications.

The functional group 108 include hydroxyl groups, amine groups, thiolate groups, alkenes, n-alkenes, alkalines, N-Hydroxysuccinimide (NHS)-activated esters, polyaniline, aminosilane groups, silanized oxides, oligothiophenes, and diazonium compounds. A hydroxyl group is a moiety with the formula OH. It contains oxygen bonded to hydrogen. Hydroxyl groups are present on some polysaccharides such as agarose. An amine group is an organic hydrocarbon that contains a basic nitrogen atom with a lone pair of electrons. Amines are derivatives of ammonia in which one or more hydrogen atoms are replaced by a substituent such as an alkyl or aryl group (i.e., alkylamines and arylamines; amines in which both types of substituent are attached to one nitrogen atom are called alkylarylamines). Amines can be classified according to the nature and number of substituents on nitrogen. Aliphatic amines contain only hydrogen and alkyl substituents. Aromatic amines have the nitrogen atom connected to an aromatic ring.

A thiolate group is any organosulfur compound of the form R—SH, where R represents an alkyl or other organic substituent. An alkene is an unsaturated hydrocarbon that contains at least one carbon-carbon double bond. A n-alkene is an unsaturated linear hydrocarbon. An alkyne is an unsaturated hydrocarbon containing at least one carbon-carbon triple bond.

An NHS-activated ester is reactive species which couples with amines efficiently. A silanized oxide is an oxide of silicon that forms a covalent —Si—O—Si— bonds. Polyaniline (PANI) is a conducting polymer of the semi-flexible rod polymer family. An oligothiophene is oligomer of a thiophene. Diazonium compounds are a group of organic compounds with the structure R—$N^+_2X^-$ where R can be any organic group, such as an alkyl or an aryl (e.g., aryl diazonium), and X is an inorganic or organic anion, such as a halogen.

Figure 2:
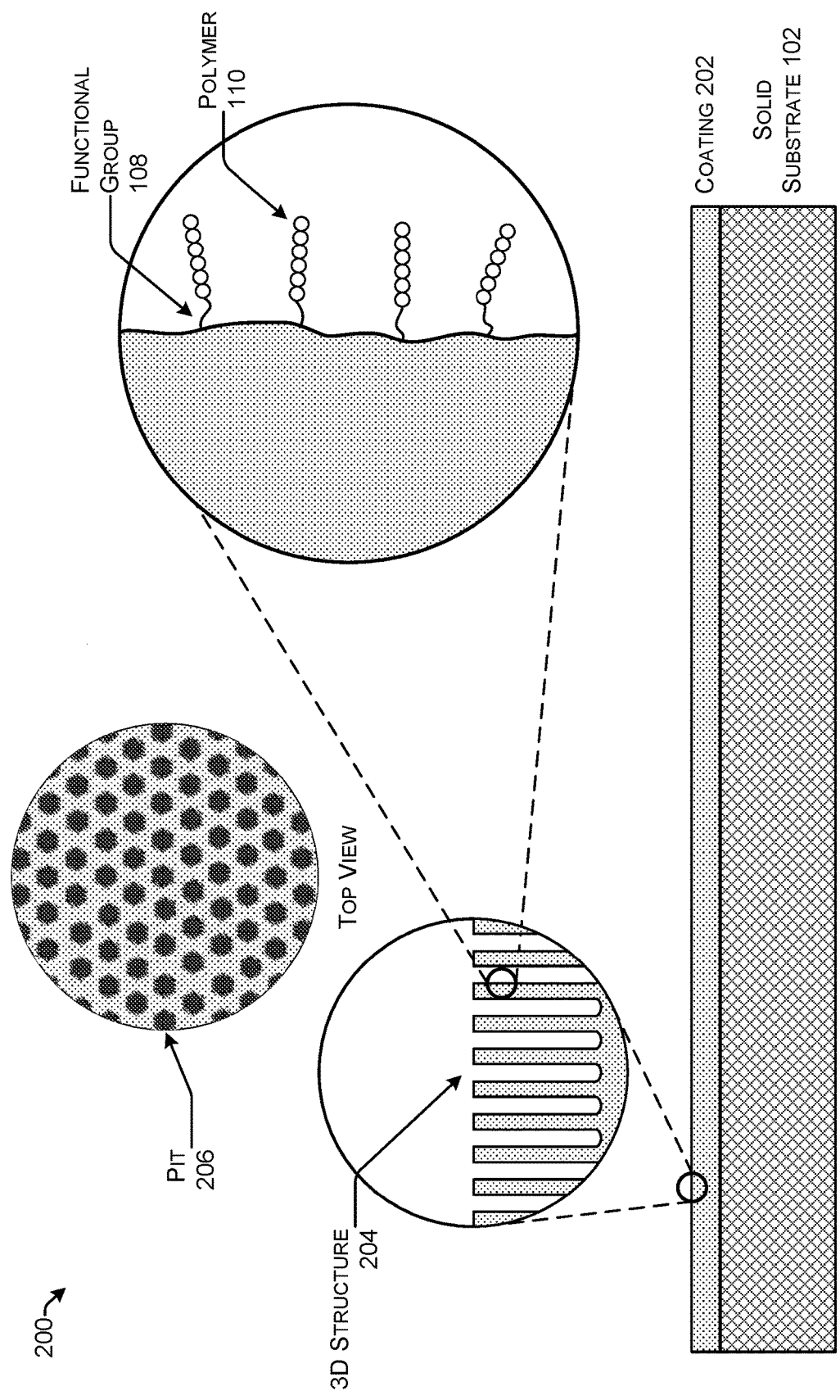
FIG. 2 shows one example of a stack for solid-phase polymer synthesis with a coating that has a three-dimensional structure.

FIG. 2 shows one example of a stack 200 for use in solid-phase polymer synthesis with a coating 202 of porous anodic aluminum oxide (AAO). AAO has a three-dimensional structure 204 that includes many honeycomb-shaped pits 206 in the coating 202. The honeycomb-shaped pits 206 can be created by etching aluminum electrochemically with an acidic solution (e.g., phosphoric acid, chromic acid, sulfuric acid, etc.). Thus, in some configurations the solid substrate 102 is aluminum and the coating 202 is the etched surface of the same piece of metal. Alternatively, the coating 202 may be a porous AAO membrane annealed to the surface of a solid substrate 102 made from aluminum or another material such as silicon. For example, a solid substrate 102 of silicon may be sputtered with a thin layer (e.g. about 500 nm) of aluminum which is then etched to create the coating 202. Functional groups 108 can be added to porous AAO using silanization, chemical grafting, electro-grafting, photochemical grafting, electrochemical polymerization, or the like.

Figure 3:
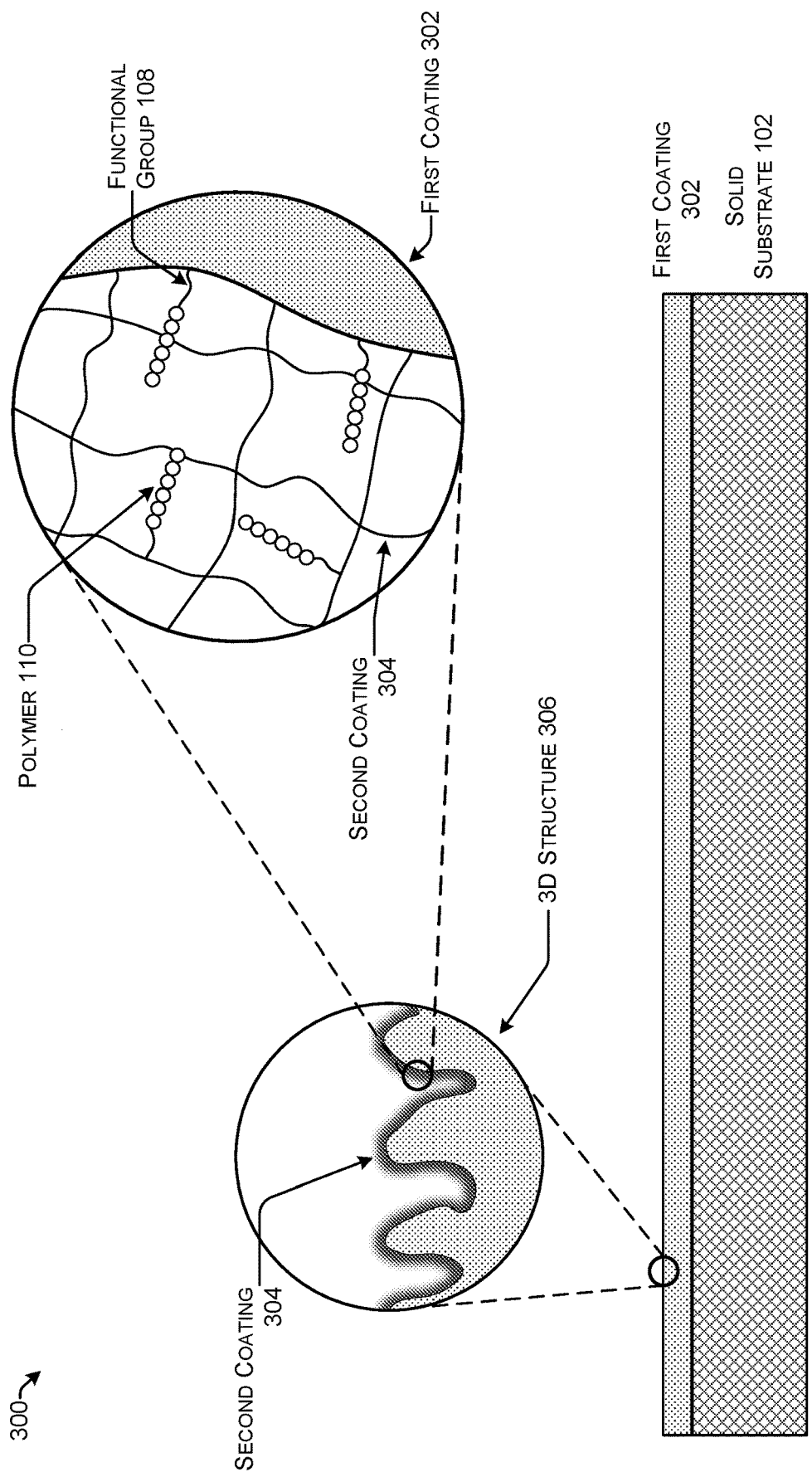
FIG. 3 shows one example of a stack for solid-phase polymer synthesis with a coating that has a three-dimensional structure and a second coating that also has a three-dimensional structure.

FIG. 3 shows one example of a stack 300 for use in solid-phase polymer synthesis with a first coating 302 and a second coating 304. The second coating 304 may be applied to the surface of the first coating 302. The second coating 304 increases the surface area more than the first coating 302 or to the solid substrate 102.

In this example stack 300, the second coating 304 is shown as an organic polymer hydrogel such as, for example, polyacrylamide hydrogel. Functional groups 108 may be available on both the first coating 302 and the second coating 304. Thus, use of a second coating 304 does not preclude attachment of the polymers 110 to the first coating 302.

Figure 4:
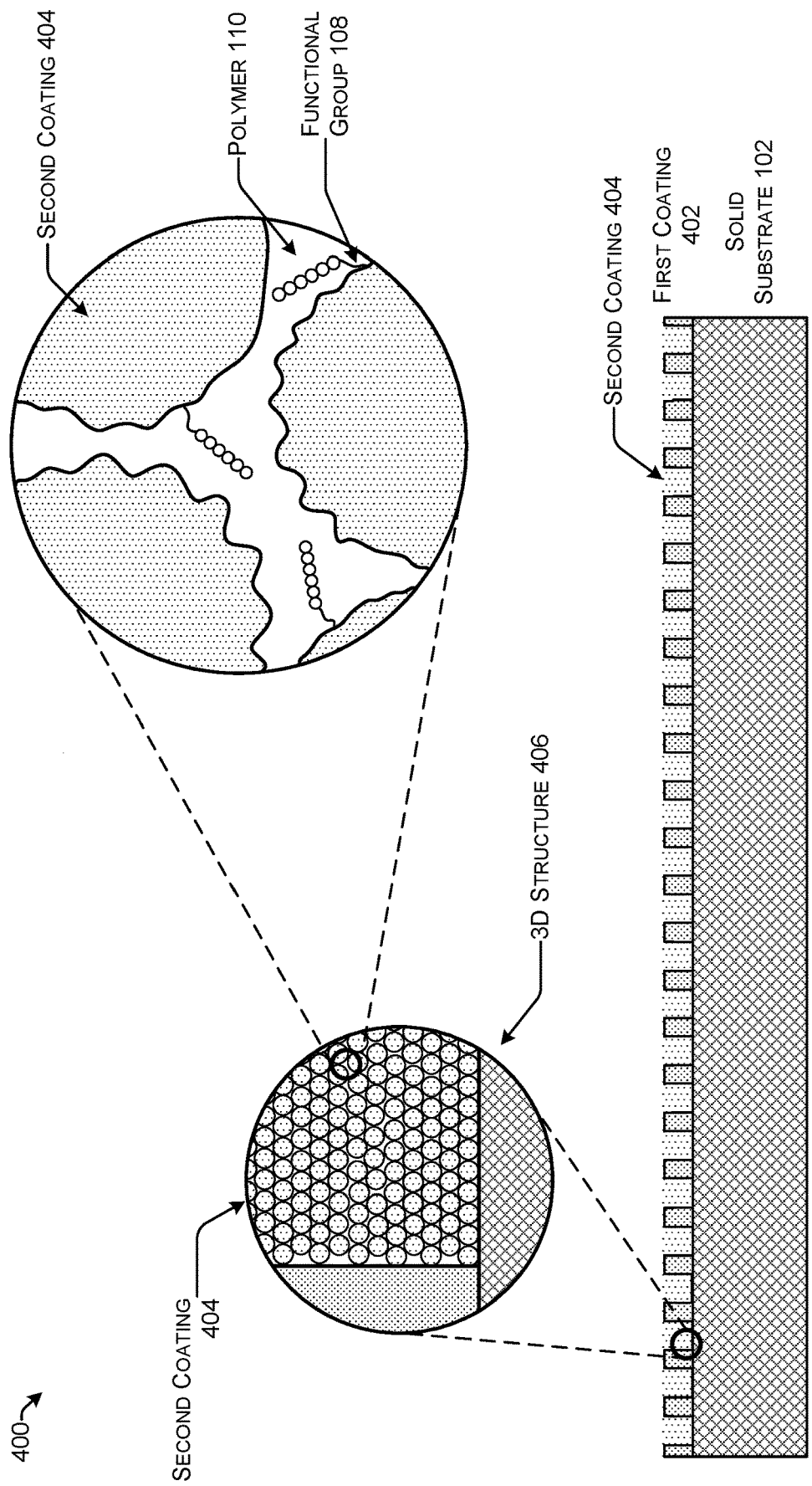
FIG. 4 shows one example of a stack for solid-phase polymer synthesis with a coating that has a three-dimensional structure and a second coating that also has a three-dimensional structure.

FIG. 4 shows one example of a stack 400 for use in solid-phase polymer synthesis with a first coating 402 that is patterned and a second coating 404. Metals are one type of material that may be patterned to form the first coating 402. In this example stack 400, the second coating 404 is illustrated as microparticles. The microparticles may be formed from silicon, glass, polystyrene, polymeric resins, latex, etc. In one implementation, the microparticles are nanospheres of silicon dioxide with diameters of about 50-200 nm.

The stack 400 may be coated with the microparticles following patterning of the first coating 402. Microparticles may be deposited by techniques such as spin coating, dip coating, spray coating, etc. The patterning of the first coating 402 can create separate wells or regions on the surface of the stack 400 that may be exposed to different reaction conditions and used to synthesize polymers with different sequences.

Figure 5:
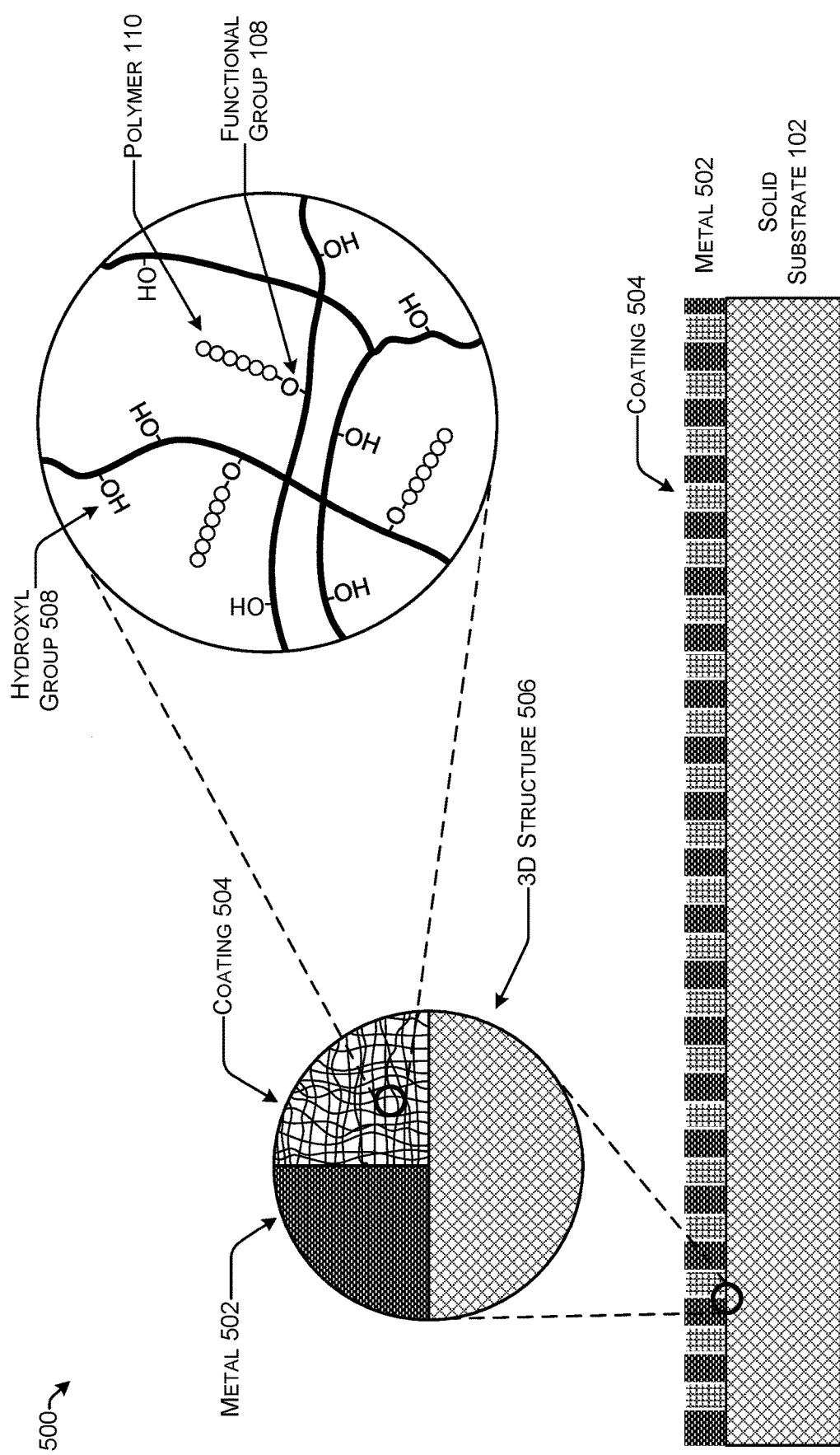
FIG. 5 shows one example of a stack for solid-phase polymer synthesis with a patterned solid substrate and a coating that has a three-dimensional structure.

FIG. 5 shows one example of a stack 500 for use in solid-phase polymer synthesis that is patterned with a metal 502 (e.g., a noble metal). The metal 502 is patterned on the surface of the solid substrate 102 using techniques such as photolithography. Patterning or etching may expose the metal such as by use of a photoresist layer on top of the metal 502 (not shown).

The coating 504 covers the solid substrate 102 in the spaces exposed by the patterning. In this example stack 500, the coating 504 is shown as agarose or other organic polymer. The coating 504 may be applied by spin coating. The three-dimensional structure 506 is provided by the mesh of the organic polymers in the coating 504. Organic polymers such as agarose include free hydroxyl groups 508 that can serve as functional groups 108. Thus, a separate functionalization step is not necessary for this coating 504.

Figure 6:
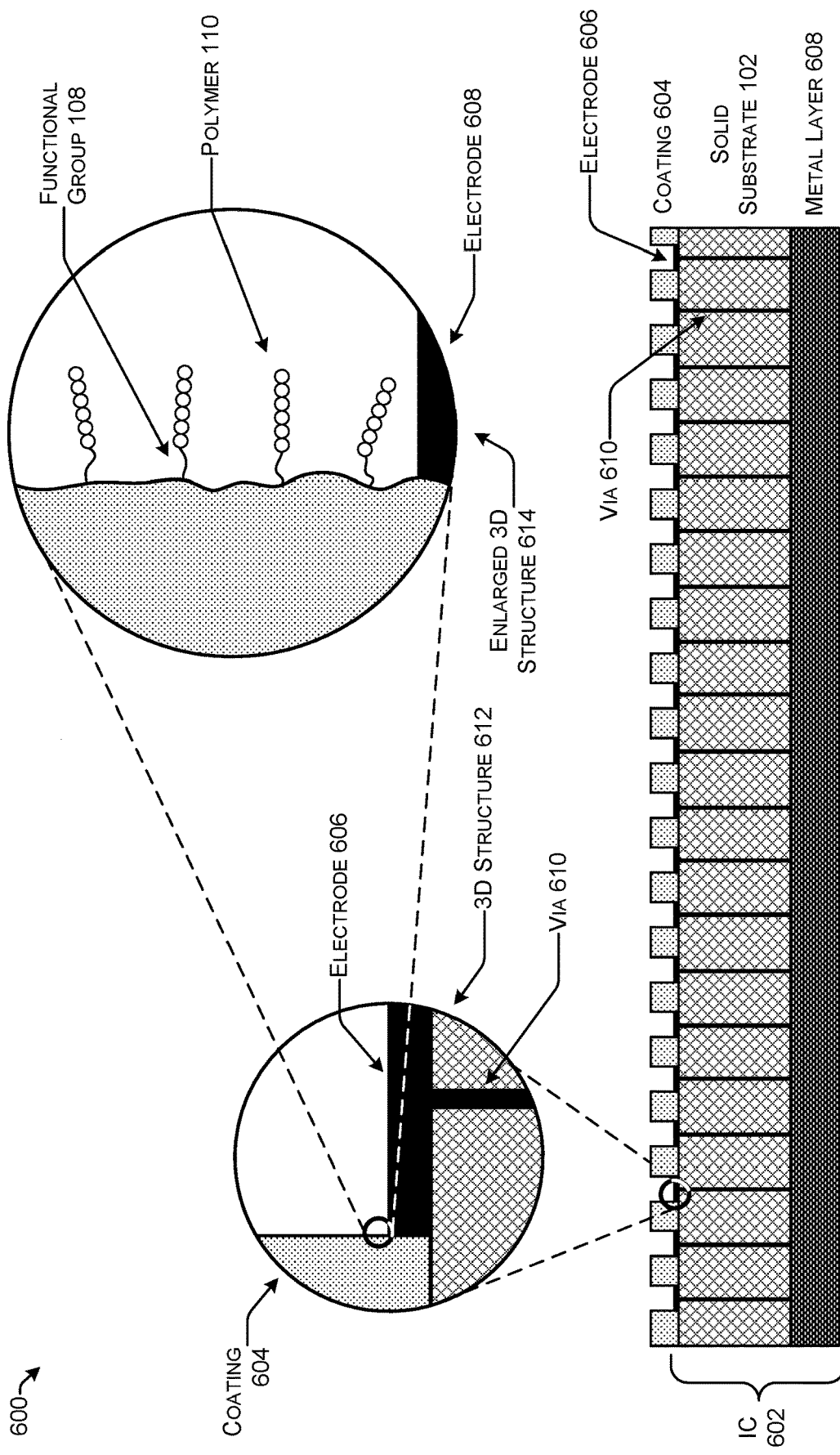
FIG. 6 shows one example of a stack for solid-phase polymer synthesis with a solid substrate that includes an integrated circuit with electrodes and a patterned coating that has a three-dimensional structure.

FIG. 6 shows one example of a stack 600 for use in solid-phase polymer synthesis that includes an integrated circuit (IC) 602. The stack 600 includes a solid substrate 102 formed from a semiconductor typically, but not exclusively, silicon. The coating 604 covering the solid substrate 102 is patterned exposing one or more electrodes 606 deposed on the surface of the solid substrate 102. The solid substrate 102 may contain one or more metal layers 608 that implement the connections of the IC 602. The metal layers 608 are deposed below and/or embedded within the solid substrate 102. A via 610 provides an electrical connection between the electrode 606 and one of a metal layer 608. The solid substrate 102 may contain additional vias 610 connecting electrodes 606 to other metal layers that are not shown. The three-dimensional structure 612 illustrates details the configuration of components on the surface of the stack 600. The enlarged three-dimensional structure 614 illustrates attachments of polymers 110 to the coating 604 in close proximity to the electrode 606.

The IC 602 may be implemented as one of any number of different types of integrated circuits such as, but not limited to, a CMOS integrated circuit or a layered silicon-insulator-silicon (SOI) substrate. CMOS circuits use a combination of p-type and n-type metal-oxide-semiconductor field-effect transistor (MOSFETs) to implement logic gates and other digital circuits. Commercial CMOS products are integrated circuits composed of up to billions of transistors of both types, on a rectangular piece of silicon of between 10 and 400 mm$^2$. A series of controllable gates/transistors implemented with CMOS circuits can be controlled to inject charge at any electrode 606 on the solid substrate 102.

SOI-based circuits differ from conventional silicon-built circuits in that the silicon junction is above an electrical insulator, typically silicon dioxide. An SOI MOSFET is a semiconductor device in which a semiconductor layer such as silicon or germanium is formed on an insulator layer which may be a buried oxide (BOX) layer formed in a semiconductor substrate. The insulator layer creates isolation between a p-well process and an n-well process allowing separate voltages to be applied to each.

All of the electrodes 606 in the IC 602 may be electrically coupled thereby functioning as a single electrode. Alternatively, each electrode, or groups of electrodes, may be independently addressable allowing the creation of arbitrary and variable voltage microenvironments across the surface of the solid substrate 102. This type of IC 602 may be referred to as a "microelectrode array." Electrodes 606 on the scale of a microelectrode array may be referred to as "microelectrodes." The microelectrode density may be approximately 1000 microelectrodes/cm$^2$, approximately 10,000 microelectrodes/cm$^2$, or a different density. One example of a microelectrode array is provided in Bo Bi et al., *Building Addressable Libraries: The Use of "Safety-Catch" Linkers on Microelectrode Arrays*, 132 J. Am. Chem. Soc. 17,405 (2010).

The IC 602 may be coupled to a power source for powering the electrodes 606 and to control circuitry for directing the current to specified ones of the electrodes 606. The electrodes 606 may be used to create the coating 604 through electroplating or by creating pores in a dialectric material. Some techniques for polymer synthesis may be regulated using the electrodes 606. The electrodes 606 may also be used after synthesis is complete to cleave the polymers 110 from the coating. Examples of using microelectrode arrays in solid-phase synthesis of polymers are described in U.S. patent application Ser. No. 16/435,363 filed on Jun. 7, 2019 with the title "Reversing Bias In Polymer Synthesis Electrode Array."

In some implementations, the coating 604 may also function as a passivation coating that forms a non-reactive seal and provides electrical isolation of the electrodes 606. Silicon dioxide is one example of a coating 604 that can form a passivation coating.

Figure 7:
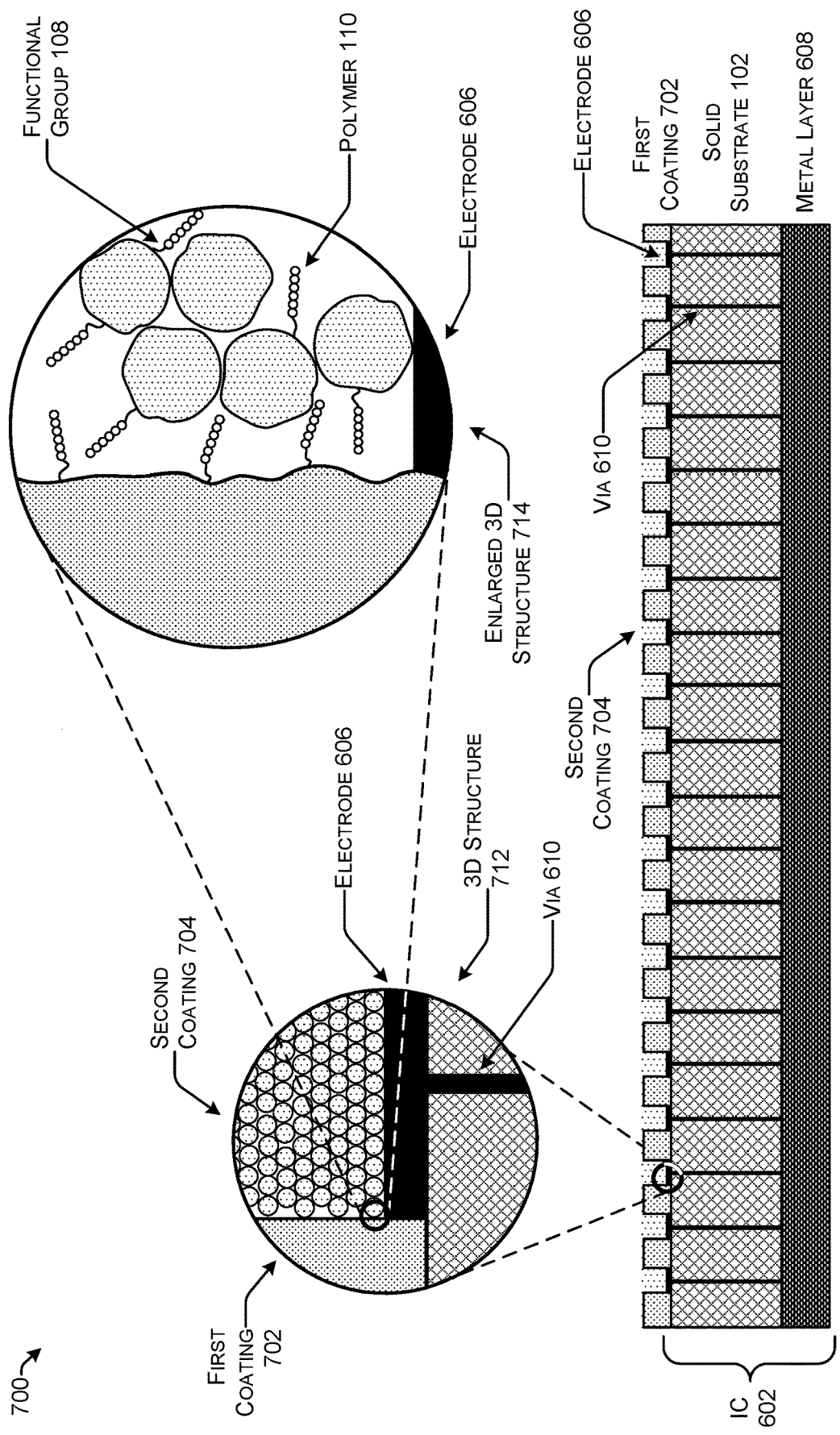
FIG. 7 shows one example of a stack for solid-phase polymer synthesis with a solid substrate that includes an integrated circuit with electrodes and a patterned coating that has a three-dimensional structure and a second coating.

FIG. 7 shows one example of a stack 700 for use in solid-phase polymer synthesis that includes an integrated circuit (IC) 602. Stack 700, like stack 600, includes a solid substrate 102 formed from a semiconductor, one or more electrodes 606 deposed on the surface of the solid substrate 102, one or more metal layers 608 beneath are embedded within the solid substrate 102, and one or more vias 610 connecting the electrode 606 to the metal layer 608.

Stack 700 includes a first coating 702 covering the solid substrate 102 that is patterned to expose the electrodes(s) 606 deposed on the surface of the solid substrate 102. Stack 700 differs from stack 600 due to the addition of a second coating 704. The compositions and the relationship of the first coating 702 and the second coating 704 may be the same or similar to the dual coatings illustrated in FIGS. 3 and 4. For example, the first coating 702 may be a metal oxide, a high-κ dielectric, a low-κ dielectric, an etched metal, a carbon material, an organic polymer, or combinations thereof. The second coating 704 may be formed from any of microparticles, aerogels, and organic polymers.

The three-dimensional structure 712 of stack 700 shows the first coating 702 and the second coating 704 in proximity to the electrode 606. The enlarged three-dimensional structure 714 illustrates attachment of polymers 110 to both the first coating 702 and the second coating 704.

Illustrative Process

For ease of understanding, the process discussed in this disclosure is delineated as separate operations represented as independent blocks. However, these separately delineated operations should not be construed as necessarily order dependent in their performance. The order in which the processes described is not intended to be construed as a limitation, and unless other otherwise contradicted by context any number of the described process blocks may be combined in any order to implement the process or an alternate process. Moreover, it is also possible that one or more of the provided operations is modified or omitted.

Figure 8:
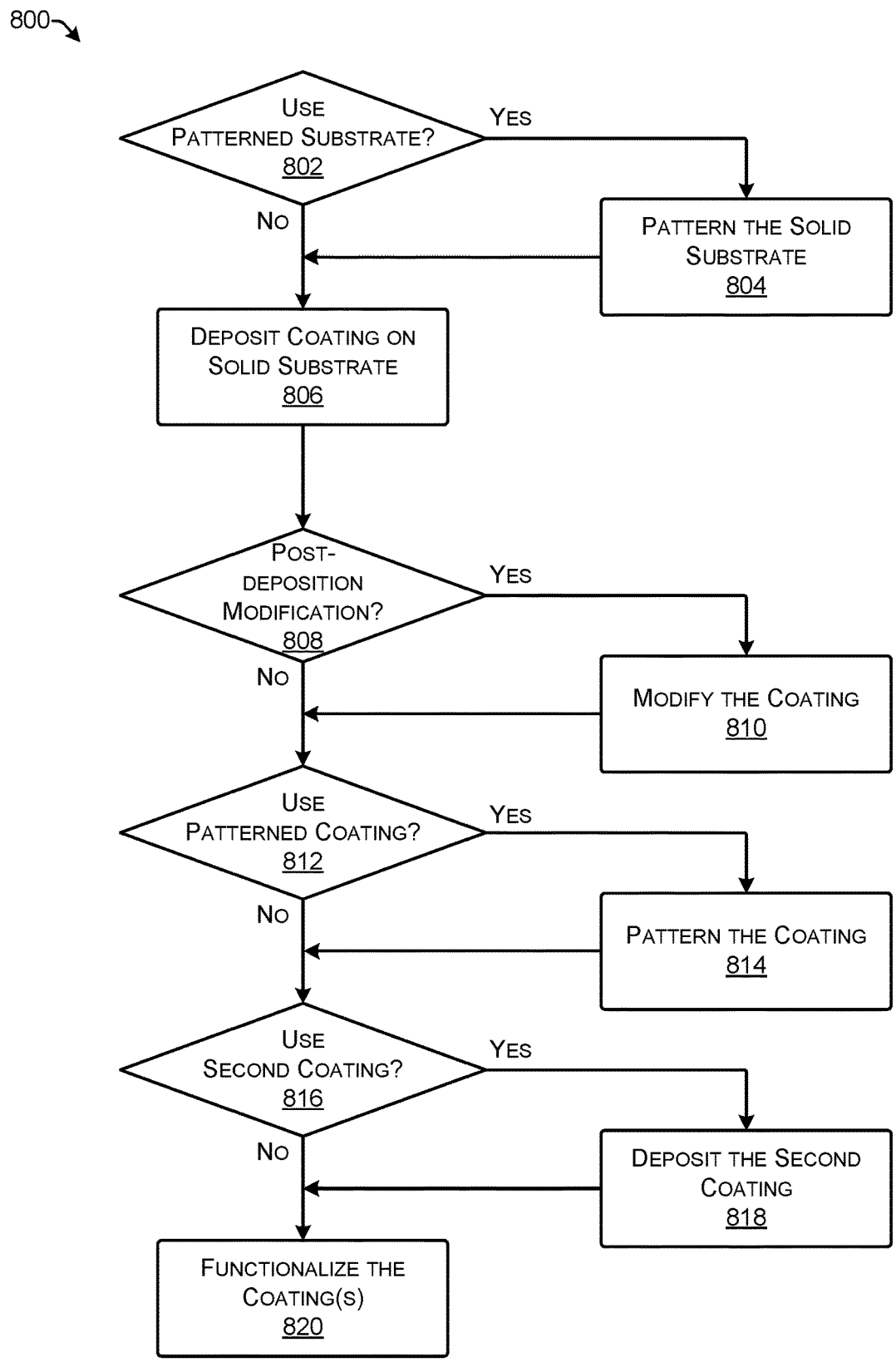
FIG. 8 is a flow diagram showing an illustrative process for creating a stack for use with solid-phase polymer synthesis.

FIG. 8 shows process 800 for creating a stack for use with solid-phase polymer synthesis. Process 800 may be used to create any of the stacks shown in FIGS. 1-6.

At 802, process 800 varies depending on if a patterned substrate is used to make the stack. If a patterned substrate is used, process 800 proceeds along the "yes" path to 804; if it does not, process 800 proceeds along the "no" path to 806.

At 804, the solid substrate is patterned. The solid substrate may be any of the types of solid substrates discussed in this disclosure. Patterning the solid substrate is performed by (i) selectively depositing a noble metal on the surface of the solid substrate or (ii) covering the solid substrate with a noble metal and selectively removing the noble metal by etching. The patterning may remove portions of the solid substrate thereby exposing electrodes either within the solid substrate or located below the solid substrate.

At 806, a coating is deposited on the surface of the solid substrate. The coating may be any of the types of coatings discussed in this disclosure. The coating may be applied by a number of techniques including, but not limited to, oxidizing, electroplating, annealing, spin coating, dip coating, spray coating, sputtering, in-situ polymerization, and the sol-gel process.

Electroplating is a process that uses an electric current to reduce dissolved metal cations so that they form a thin coherent metal coating on an electrode. In some implementations, if the solid substrate is a conductive material such as a metal, the entire solid substrate may be a cathode that is electroplated. In other implementations, such as when the solid substrate has electrodes on its surface, as shown in FIG. 6, those electrodes may be used for electroplating even if the solid substrate is not made of a conductive material. Electroplating includes electrodeposition which can be used to grow metals and conducting metal oxides with control over the morphology of the nanostructure by adjusting electrochemical parameters.

Spin coating is a procedure used to deposit uniform thin films onto flat substrates. Usually a small amount of coating material is applied on the center of the substrate, which is either spinning at low speed or not spinning at all. The substrate is then rotated at high speed in order to spread the coating material by centrifugal force. A machine used for spin coating is called a spin coater. Spin coating is used in microfabrication of functional oxide layers on glass or single crystal substrates using sol-gel precursors, where it can be used to create uniform thin films with nanoscale thicknesses. Spin coating is also used in photolithography to deposit layers of photoresist about 1 μm thick.

Dip coating is a coating process which is used to create thin-film coatings. For coating an object such as a solid substrate, it can be simply inserted and removed from a bath of coating. The dip coating technique is used for making thin films by self-assembly and with the sol-gel technique. Self-assembly can give film thicknesses of exactly one monolayer. The sol-gel technique creates thicker films with a precisely controlled thickness that is mainly determined by the deposition speed and solution viscosity.

Sputtering is a phenomenon in which microscopic particles of a solid material are ejected from its surface after the material is itself bombarded by energetic particles of a plasma or gas. Sputter deposition is a physical vapor deposition (PVD) method of depositing thin films that involves eroding material from a target source onto a solid substrate. Sputtering deposition usually uses an argon plasma because argon, a noble gas, will not react with the target material. Sputtering may be used to deposit metal oxides.

The sol-gel process is a method for producing solid materials from small molecules. In this process, a "sol" (a colloidal solution) is formed that then gradually evolves towards the formation of a gel-like diphasic system containing both a liquid phase and solid phase with morphologies ranging from discrete particles to continuous polymer networks. The precursor sol can be deposited on a solid substrate to form a film (e.g., by dip-coating or spin coating) and then dried to remove the remaining liquid.

One example of the sol-gel process is the Stöber process. The Stöber process is a chemical process used to prepare silicon dioxide particles of controllable and uniform size. A molecular precursor (typically tetraethylorthosilicate) is reacted with water in an alcoholic solution and the resulting molecules then join together to build larger structures. The reaction produces silicon dioxide particles with diameters ranging from 50-2000 nm, depending on conditions. The Stöber process may be used to prepare silicon dioxide microparticles and silicon dioxide aerogels.

Some techniques for applying the coating involve structurally or chemically modifying the top surface of the solid substrate. For example, the solid substrate may be a made of a material that can be treated (e.g., oxidized) to provide an outer metal oxide surface material. For example, the surface of a silicon or aluminum substrate may be oxidized to provide a silicon dioxide or aluminum dioxide coating.

At 808, process 800 varies depending on if the coating is modified after being deposited on the surface of the solid substrate. If there are post-deposition modifications, process 800 proceeds along the "yes" path to 810; if not, process 800 proceeds along the "no" path to 812.

At 810, the coating is modified while it is deposited on the surface of the solid substrate. One type of modification is cross-linking of polymers in the coating formed from organic polymers such as a hydrogel.

At 812, process 800 varies depending on if the coating is patterned. If the coating is patterned, process 800 proceeds along the "yes" path to 814; if not, process 800 proceeds along the "no" path to 816.

At 814, the coating is patterned. Patterning of a coating includes photolithography which may be performed using techniques known to those of skill in the art in view of the contents of this disclosure. Examples of coatings that may be patterned include metals, metal oxides, and carbon-containing compounds. Patterning of the coating can be used to create physical isolation between spots of the polymers being synthesized. This can improve the quality of the resulting polymers by keeping polymers synthesized adjacent spots separate from each other. Separation of polymers can improve fidelity by reducing cross-contamination between groups of polymers being synthesized with different sequences.

At 816, process 800 varies depending on if a second coating is applied to the stack. If a second coating is applied, process 800 proceeds along the "yes" path to 818; if not, process 800 proceeds along the "no" path to 820.

At 818, a second coating is applied to the stack. The second coating may be applied by techniques including, but not limited to, annealing, spin coating, dip coating, spray coating, sputtering, and the sol-gel process.

At 820, the coating, and second coating if present, are functionalized. Functionalization adds functional groups that bond to monomers of a polymer being synthesized on the stack. Functional groups may be attached to the coating by silanization, chemical grafting, electro-grafting, photo-chemical grafting, electrochemical polymerization, or other techniques.

A coating can be functionalized with a self-assembled monolayer. Self-assembled monolayers of organic molecules are molecular assemblies formed spontaneously on surfaces by adsorption and are organized into more or less large ordered domains. The molecules possess a head group that has a strong affinity to the surface and anchors the molecule. Common head groups include thiols, silanes, phosphonates, etc. In one implementation, a gold coating is functionalized by a self-assembled monolayer of thiolate linkers.

Coatings can also be functionalized by chemical grafting. Grafting, in the context of polymer chemistry, refers to the addition of polymer chains onto a surface. Chemical grafting techniques include hydrosilylation. Chemical grafting may be used, for example, to add carbon-containing groups (e.g., alkenes, n-alkenes, alkynes, or the like), NETS-activated esters, silanized oxides, and the like. Hydrosilylation is one example of chemical grafting. Hydrosilylation, also called catalytic hydrosilation, describes the addition of Si—H bonds across unsaturated bonds. Ordinarily the reaction is conducted catalytically and usually the substrates are unsaturated organic compounds. Alkenes and alkynes give alkyl and vinyl silanes; aldehydes and ketones give silyl ethers.

Electro-grafting refers to the electrochemical reaction that permits organic layers to be attached to solid conducting services. Electro-grafting can add aryl diazononium linkers or oligothiophene groups to conductive metals (e.g., gold, platinum, and silicon). Diazonium linkers may be added to a carbon material by electro-grafting. Electro-grafting may also be used for electrochemical initiated polymerization of polyaniline.

Photochemical grafting can be used to add n-alkenes with terminal functional groups onto carbon material. Photochemical grafting uses photochemical reactions initiated by ultraviolet light to functionalized surfaces such as carbon, diamond, and carbon nanofibers.

Functional groups may also be synthesized directly on the surface of the coating by reversible addition-fragmentation chain-transfer polymerization ("RAFT"). RAFT polymerization is one of several kinds of reversible-deactivation radical polymerization. It makes use of a chain transfer agent in the form of a thiocarbonylthio compound (or similar, referred to as a RAFT agent) to provide control over the generated molecular weight and polydispersity during a free-radical polymerization.

Electrochemical polymerizations are performed by using a three electrode system involving the counter, reference, and working electrodes. During the electrochemical polymerization process, an anodic potential is applied to the monomer to oxidize onto the electrode, and it initiates polymerization. Polymer films with a desired thickness may be obtained by controlling the number of cycles or the current that is applied to the electrode.

Functionalization may not be necessary for some types of coatings such as polysaccharides (e.g., agarose) and metal oxides. However, even if the coating is a metal oxide material, it can be further functionalized to create a silanized region or layer that is patterned on or substantially covers the metal oxide material. Mineral components like glass and metal oxide surfaces can all be silanized because they contain hydroxyl groups which attack and displace the alkoxy groups on the silane thus forming a covalent —Si—O—Si— bond. The silanized region or layer can comprise a plurality of silyl groups that individually are attached to a terminal alcohol, amino group, epoxide group, or a combination thereof. The silyl group may be a glycidoxipropylt-rimetiloxisilane, a silyl alcohol, or a silyl amine. Such groups can be provided by silanization techniques known to those of ordinary skill in the art with the benefit of the present disclosure and can be used to chemically graft functional group on to the coating.

Following functionalization, a stack created by process 800 may be used to synthesize polymers. However, some types of stacks may be incompatible with certain synthetic techniques. For example, the phosphoramidite method of synthesizing DNA uses harsh chemicals including acetonitrile which can damage some types of coatings such as organic polymers (e.g., agarose).

Upon completion of synthesis, the polymers may be separated from the stack by cleaving linkers which may be the functional groups or coupled to the functional groups. The linkers may be cleaved by any conventional technique (appropriate for the type of linker) known to those of ordinary skill in the art. The substrate can then then be washed removing the polymers. The polymers may be processed further or stored.

Example Stacks

Example 1: An illustrative stack includes a solid substrate formed from silicon. The silicon substrate is sputtered with a thin layer of aluminum forming a coating of aluminum oxide that is about 500 nm thick. The coating is electro-chemically etched with an acidic solution to create porous AAO. The silicon substrate is patterned with a noble metal such as platinum or gold. The functional groups are attached to the AAO by silanization through submerging the whole stack in a 2% v/v 3-aminopropyltriethoxysilane in ethanol for about 8-16 hours followed by baking at 100° C. for two about hours.

Example 2: An illustrative stack includes a solid substrate formed from silicon. The silicon substrate is patterned with a noble metal such as platinum or gold. The coating is SNOWTEX-UP colloidal silica nanoparticles which are available from Nissan Chemical. SNOWTEX-UP has an elongated shape unlike spherical silicasol. SNOWTEX-UP is 20-21% silicon dioxide by weight with a narrow dimension of about 9-15 nm and a long dimension of about 40-100 nm. SNOWTEX-UP is an example of a silicon dioxide nanoparticle. SNOWTEX-UP (20% by weight) in isopropanol is spin coated at 2000 RPM for 60 seconds onto the silicon substrate. This formed a layer of approximately 1 μm thick as measured by atomic force microscopy with pore sizes between about 20-50 nm. The stack is then baked at 100° C. overnight which forms a porous silicon dioxide coating on top of the silicon substrate. The functional groups are attached by silanization through submerging the whole stack in a 2% v/v 3-aminopropyltriethoxysilane in ethanol for about 8-16 hours followed by rinsing the stack and then baking at 100° C. for about two hours.

Example 2-1: This illustrative stack is a modification of the stack of Example 2 that replaces silicon dioxide nanoparticles with a silicon dioxide aerogel. The aerogel is created by the Stöber process. Stöber silicon dioxide aerogels can have a specific surface area of 700 m² g⁻¹ and a density of 0.040 g cm⁻³. Other aspects of this stack are the same as Example 2.

Example 3: An illustrative stack includes a solid substrate formed from silicon. The silicon substrate is patterned with platinum strips. The coating is created by spin coating an agarose solution (3% by weight) in 1×TE buffer at 2000 RPM for 60 seconds under a nitrogen atmosphere. TE buffer is a solution of about 10 parts tris(hydroxymethyl)aminomethane (TRIS) to one part ethylenediaminetetraacetic acid (EDTA). The stack is then baked at about 100° C. for at least two hours including up to about 8-16 hours. Free hydroxyl groups in the agarose provide the functional groups, so a separate functionalization step is not needed.

Example Yields

Using conventional solid phase synthesis procedures with a 50 nmol universal synthesis CPG packed column with 1000 Å particles, the DNA yield is approximately 2000 ng/μL for a total of about 40,000 ng of DNA in 20 μL of recovered eluent. Synthesis on a silanized glass slide with a surface area of 137 mm² is predicted to yield up to 400 ng of DNA assuming that a single ssDNA molecule uses 16 nm² of surface area and the DNA strands are 89 nt long.

Tests with the same size of glass slide coated with SNOWTEX-UP colloidal silica nanoparticles synthesizing 89 nt long ssDNA molecules produced about 16,000 ng of DNA. This yield from the coated glass slide is about 40× greater than the theoretical yield for the uncoated slide. The coating on the glass slide used about ⅓ of the number of particles as the CPG column. One-third of the yield from the CPG column is about 13,333 ng of DNA. Thus, synthesis on a solid substrate coated with silica nanoparticles provides approximate 1.2× higher DNA yield than a CPG column containing the same number of particles. Additionally, it provides rigid structure with a flat, but textured, surface rather than a column or porous frit. This increases the ease of handling of the solid substrate which is particularly advantageous for automated processing.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A stack for solid-phase polymer synthesis comprising: a solid substrate (102); a coating (104) that has a three-dimensional structure (106) which increases available surface area relative to the solid substrate, the coating covering at least a portion of the solid substrate; and a functional group (108) attached to the coating.

Clause 2. The stack of clause 1, further comprising a polymer (110) covalently bound to the functional group, wherein the polymer is comprised of an oligonucleotide or a polypeptide.

Clause 3. The method of clause 2, wherein the polymer is comprised of an oligonucleotide and the oligonucleotide has a sequence that encodes digital information.

Clause 4. The stack of any of clauses 1-3, wherein the solid substrate comprises a silicon material.

Clause 5. The stack of any of clauses 1-3, wherein the solid substrate comprises a metal material.

Clause 6. The stack of any of clauses 1-3, wherein the solid substrate comprises a plastic.

Clause 7. The stack of any of clauses 1-6, wherein the solid substrate is not glass.

Clause 8. The stack of any of clauses 1-7, wherein the solid substrate is patterned with a metal (502).

Clause 9. The stack of stack of any of clauses 1-8, wherein the solid substrate comprises a portion of an integrated circuit (602).

Clause 10. The stack of clause 9, wherein the integrated circuit comprises a complementary metal-oxide-semiconductor (CMOS) integrated circuit.

Clause 11. The stack of any of clauses 1-10, wherein the coating comprises a metal oxide.

Clause 12. The stack of any of clauses 1-10, wherein the coating comprises an etched metal (202).

Clause 13. The stack of any of clauses 1-10, wherein the coating comprises a high-κ dialectric.

Clause 14. The stack of any of clauses 1-10, wherein the coating comprises a low-κ dialectric.

Clause 15. The stack of any of clauses 1-10, wherein the coating comprises a carbon material.

Clause 16. The stack of any of clauses 1-10, wherein the coating comprises an organic polymer (504).

Clause 17. The stack of any of clauses 1-16, wherein a structure of the coating is a thin film.

Clause 18. The stack of any of clauses 1-16, wherein a structure of the coating is a hydrogel (304).

Clause 19. The stack of any of clauses 1-16, wherein a structure of the coating is a microparticle (404).

Clause 20. The stack of any of clauses 1-19, wherein the coating is patterned (402) exposing the solid substrate.

Clause 21. The stack of any of clauses 1-20, wherein the coating increases available surface area relative to the solid substrate by factor of at least 1.1.

Clause 22. The stack of any of clauses 1-20, wherein the coating increases available surface area relative to the solid substrate by factor of at least 1.5.

Clause 23. The stack of any of clauses 1-20, wherein the coating increases available surface area relative to the solid substrate by factor of at least 3.

Clause 24. The stack of any of clauses 1-23, further comprising a second coating (304; 404) which further increases the available surface area relative to the coating.

Clause 25. The stack of clause 24, wherein the second coating comprises microparticles (404).

Clause 26. The stack of clause 24, wherein the second coating comprises aerogels.

Clause 27. The stack of clause 24, wherein the second coating comprises organic polymers (504).

Clause 28. The stack of any of clauses 1-27, wherein the functional group comprises a hydroxyl group (508).

Clause 29. The stack of any of clauses 1-27, wherein the functional group comprises an amine group.

Clause 30. The stack of any of clauses 1-27, wherein the functional group comprises a thiolate group.

Clause 31. The stack of any of clauses 1-27, wherein the functional group comprises an alkene.

Clause 32. The stack of any of clauses 1-27, wherein the functional group comprises, a n-alkene.

Clause 33. The stack of any of clauses 1-27, wherein the functional group comprises an alkaline.

Clause 34. The stack of any of clauses 1-27, wherein the functional group comprises a N-Hydroxysuccinimide (NHS)-activated ester.

Clause 35. The stack of any of clauses 1-27, wherein the functional group comprises polyaniline.

Clause 36. The stack of any of clauses 1-27, wherein the functional group comprises, a silanized oxide.

Clause 37. The stack of any of clauses 1-27, wherein the functional group comprises, an oligothiophene.

Clause 38. The stack of any of clauses 1-27, wherein the functional group comprises a diazonium compound.

Clause 39. An oligonucleotide synthesizer comprising the stack of any of clauses 1-38.

Clause 40. A method of solid-phase synthesis of oligonucleotides with the oligonucleotide synthesizer of clause 39 using the phosphoramidite method or enzymatic synthesis.

Clause 41. A stack for solid-phase polymer synthesis comprising: a silicon substrate (102) patterned with a noble metal (502); a coating (104) that has a three-dimensional structure with an available surface area that is greater than the silicon substrate, the coating selected from the group comprising silicon dioxide, aluminum oxide, porous anodic aluminum oxide (AAO) (202), and agarose (504); and a functional group (108) present on the coating, the functional group selected from the group comprising an aminosilane group and a hydroxyl group (508).

Clause 42. The stack of clause 41, wherein the coating comprises the porous AAO (202) and the functional group comprises the aminosilane group.

Clause 43. The stack of clause 41, wherein the coating comprises silicon dioxide microparticles and the functional group comprises the aminosilane group.

Clause 44. The stack of clause 41, wherein the coating comprises agarose (504) and the functional group comprises the hydroxyl group (508) present on the agarose as a free hydroxyl group.

Clause 45. An oligonucleotide synthesizer comprising the stack of any of clauses 41-44.

Clause 46. A method of solid-phase synthesis of oligonucleotides with the oligonucleotide synthesizer of clause 45 using the phosphoramidite method or enzymatic synthesis.

Clause 47. A method of making a stack for solid-phase polymer synthesis comprising: depositing a coating (104) having a three-dimensional structure (106) on a solid substrate (102), the coating having an available surface area that is greater than the solid substrate; and functionalizing the coating with a functional group (108) that forms a covalent bond to a monomer subunit of a polymer (110).

Clause 48. The method of clause 47, wherein the depositing the coating comprises electroplating.

Clause 49. The method of clause 47, wherein the depositing the coating comprises annealing.

Clause 50. The method of clause 47, wherein the depositing the coating comprises spin coating.

Clause 51. The method of clause 47, wherein the depositing the coating comprises dip coating.

Clause 52. The method of clause 47, wherein the depositing the coating comprises spray coating.

Clause 53. The method of clause 47, wherein the depositing the coating comprises sputtering.

Clause 54. The method of clause 47, wherein the depositing the coating comprises a sol-gel process.

Clause 55. The method of clause 47, wherein the solid substrate comprises an electrode (606) and the depositing the coating comprises electroplating using the electrode.

Clause 56. The method of any of clauses 47-55, further comprising patterning the solid substrate with a metal or a semiconductor.

Clause 57. The method of any of clauses 47-56, further comprising patterning the coating, wherein the coating comprises a metal, a metal oxide, or a carbon-containing compound.

Clause 58. The method of any of clauses 47-57, further comprising etching the coating, wherein the coating comprises a metal.

Clause 59. The method of any of clauses 47-58, wherein the functionalizing the coating comprises silanization.

Clause 60. The method of any of clauses 47-58, wherein the functionalizing the coating comprises chemical grafting.

Clause 61. The method of any of clauses 47-58, wherein the functionalizing the coating comprises electro-grafting.

Clause 62. The method of any of clauses 47-58, wherein the functionalizing the coating comprises, photochemical grafting.

Clause 63. The method of any of clauses 47-58, wherein the functionalizing the coating comprises electrochemical polymerization.

Clause 64. The method of any of clauses 47-63, further comprising, depositing a second coating (304; 404) on the coating, the second coating having an available surface area that is greater than the coating.

Clause 65. A method of solid-phase synthesis of a polymer comprising growing the polymer on a stack created by the method of any of clauses 47-64.

Clause 66. The method of clause 65, wherein the polymer comprises an oligonucleotide having a sequence that encodes digital information.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the," and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A stack for solid-phase polymer synthesis comprising:
   a solid substrate having a surface;
   a first coating on the surface that has a three-dimensional structure and which increases the usable surface area for polymer synthesis relative to the solid substrate, the first coating covering at least a portion of the surface of the solid substrate;
   a second coating, in contact with the first coating, which further increases the usable surface area for polymer synthesis relative to the first coating, wherein the second coating comprises microparticles baked into a porous coating; and
   a functional group attached to at least one of the first coating or the second coating.

2. The stack of claim 1, further comprising a polymer covalently bound to the functional group, wherein the polymer is comprised of an oligonucleotide or a polypeptide.

3. The stack of claim 1, wherein the solid substrate comprises a silicon material, a metal material, or a plastic.

4. The stack of claim 1, wherein the first coating comprises a metal oxide, an etched metal, a high-κ dielectric, a low-κ dielectric, a carbon material, or an organic polymer.

5. The stack of claim 1, wherein a structure of the first coating is a thin film, a hydrogel, or a microparticle.

6. The stack of claim 1, wherein the functional group comprises a hydroxyl group, an amine group, a thiolate group, an alkene, a n-alkene, an alkaline, a N-Hydroxysuccinimide (NHS)-activated ester, polyaniline, a silanized oxide, an oligothiophene, or a diazonium compound.

7. A stack for solid-phase polymer synthesis comprising:
   a silicon substrate patterned with a noble metal;
   a coating that has a three-dimensional structure with an available surface area that is greater than the silicon substrate, the coating selected from the group comprising silicon dioxide, silicon dioxide microparticles, aluminum oxide, porous anodic aluminum oxide (AAO), and agarose, wherein the coating covers the silicon substrate and does not cover the noble metal; and
   a functional group present on the coating, the functional group selected from the group comprising an aminosilane group and a hydroxyl group.

8. The stack of claim 7, wherein the coating comprises the porous AAO and the functional group comprises the aminosilane group.

9. The stack of claim 7, wherein the coating comprises silicon dioxide microparticles and the functional group comprises the aminosilane group.

10. The stack of claim 7, wherein the coating comprises agarose and the functional group comprises the hydroxyl group present on the agarose as a free hydroxyl group.

11. A method of making a stack for solid-phase polymer synthesis comprising:
    sputtering an aluminum coating on to a solid substrate;
    electrochemically etching the aluminum coating to create porous AAO, the coating having an available surface area that is greater than the solid substrate; and
    functionalizing the coating with a functional group that forms a covalent bond to a monomer subunit of a polymer.

12. The method of claim 11, further comprising patterning the solid substrate with a metal or a semiconductor.

13. The method of claim 11, wherein the functionalizing the coating comprises silanization, chemical grafting, electro-grafting, photochemical grafting, or electrochemical polymerization.

14. The method of claim 11, further comprising, depositing a second coating on the coating, the second coating having an available surface area that is greater than the coating.

15. The method of claim 14, wherein the second coating comprises nanoparticles.

16. The method of claim 13, wherein functionalizing the coating comprises silanization by submersion in 3-aminopropyltriethoxysilane in ethanol.

17. The stack of claim 1, wherein the functional group is attached to both the first coating and the second coating.

18. The stack of claim 1, wherein the second coating comprises silicon dioxide nanoparticles baked into a porous silicon dioxide coating.

19. The stack of claim 1, wherein the wherein the microparticles comprise silicon dioxide microparticles.

20. The stack of claim 1, wherein the microparticles are nanoparticles.

* * * * *